(12) United States Patent
Minami et al.

(10) Patent No.: US 12,198,797 B2
(45) Date of Patent: Jan. 14, 2025

(54) INFORMATION PROCESSING DEVICE AND MEDICAL IMAGE SYSTEM

(71) Applicant: Konica Minolta, Inc., Tokyo (JP)

(72) Inventors: Hirotake Minami, Fuchu (JP); Shinsuke Katsuhara, Kodaira (JP); Ryohei Ito, Hino (JP); Nodoka Iida, Hino (JP); Amai Shimizu, Hino (JP); Ryoichi Watanabe, Toyohashi (JP)

(73) Assignee: KONICA MINOLTA, INC., Tokyo (JP)

( * ) Notice: Subject to any disclaimer, the term of this patent is extended or adjusted under 35 U.S.C. 154(b) by 580 days.

(21) Appl. No.: 17/318,309

(22) Filed: May 12, 2021

(65) Prior Publication Data
US 2021/0358597 A1 Nov. 18, 2021

(30) Foreign Application Priority Data
May 15, 2020 (JP) ................. 2020-085921

(51) Int. Cl.
*G16H 30/20* (2018.01)
*G06N 20/00* (2019.01)
*G06T 7/00* (2017.01)
*G16H 30/40* (2018.01)
*G16H 40/20* (2018.01)
*G16H 10/60* (2018.01)
(Continued)

(52) U.S. Cl.
CPC ............ *G16H 30/20* (2018.01); *G06N 20/00* (2019.01); *G06T 7/0012* (2013.01); *G16H 30/40* (2018.01); *G16H 40/20* (2018.01); *G06T 2207/30096* (2013.01); *G16H 10/60* (2018.01); *G16H 50/20* (2018.01); *G16H 50/30* (2018.01)

(58) Field of Classification Search
CPC ......... G16H 30/20; G16H 40/63; G16H 50/20
USPC ....................................................... 382/128
See application file for complete search history.

(56) References Cited

U.S. PATENT DOCUMENTS

2002/0025172 A1* 2/2002 Tsuda .................. G03D 15/001
399/8
2003/0210813 A1* 11/2003 Oosawa ................ G06T 7/0012
382/130
(Continued)

FOREIGN PATENT DOCUMENTS

JP 2006-051198 A 2/2006
JP 2007-330514 A 12/2007
(Continued)

OTHER PUBLICATIONS

Office Action dated Jul. 11, 2023 for corresponding Japanese Application No. 2020-085921, with English translation.

*Primary Examiner* — Ajibola A Akinyemi
(74) *Attorney, Agent, or Firm* — LUCAS & MERCANTI, LLP

(57) ABSTRACT

Provided is an information processing device that is interposed between an imaging control device and an image management device in communication. The information processing device including an abnormality detector and a first hardware processor. The abnormality detector performs detection of an abnormality in a medical image received from the imaging control device. The first hardware processor that determines, based on a result of the detection by the abnormality detector, content or a destination of transmission of the medical image or the result of the detection.

8 Claims, 10 Drawing Sheets

(51) Int. Cl.
 *G16H 50/20* (2018.01)
 *G16H 50/30* (2018.01)

(56) References Cited

U.S. PATENT DOCUMENTS

| | | | | | |
|---|---|---|---|---|---|
| 2008/0058639 | A1* | 3/2008 | Sakaida | ............... | G16H 30/40 |
| | | | | | 600/425 |
| 2009/0175417 | A1* | 7/2009 | Sasano | ................. | G16H 10/60 |
| | | | | | 705/3 |
| 2013/0123603 | A1* | 5/2013 | Shin | .................... | A61B 6/465 |
| | | | | | 600/407 |

FOREIGN PATENT DOCUMENTS

| | | |
|---|---|---|
| JP | 2009-157527 A | 7/2009 |
| JP | 2017-515574 A | 6/2017 |

* cited by examiner

| DOCTOR NAME | USER ID | SPECIALTY | IMAGE INTERPRETATION ABILITY | FATIGUE LEVEL | AVAILABILITY |
|---|---|---|---|---|---|
| | | | | | |
| | | | | | |
| | | | | | |
| | | | | | |
| | | | | | |

FIG.6

| PATIENT ID | PATIENT NAME | EXAMINATION DATE AND TIME | EXAMINATION ID | MODALITY | SOP INSTANCE UID | IMAGE FILE NAME | FILE STORAGE LOCATION | ABNORMALITY DETECTION RESULT | IMAGE INTERPRETATION DOCTOR | PRIORITY | ... |
|---|---|---|---|---|---|---|---|---|---|---|---|
| | | | | | | | | | | | |
| | | | | | | | | | | | |
| | | | | | | | | | | | |
| | | | | | | | | | | | |

| PATIENT ID | PATIENT NAME | EXAMINATION DATE | ... | MALIGNANCY LEVEL |
|---|---|---|---|---|
| xxxx001 | xxxx | xxxx | ... | 0.23 |
| xxxx002 | xxxx | xxxx | ... | 0.74 |
| xxxx003 | xxxx | xxxx | ... | 0.11 |
| ⋮ | ⋮ | ⋮ | ⋮ | ⋮ |
| xxxxxxx | xxxx | xxxx | ... | ... |

FIG.10B

| PATIENT ID | PATIENT NAME | EXAMINATION DATE | ... | MALIGNANCY LEVEL |
|---|---|---|---|---|
| xxxx002 | xxxx | xxxx | ... | 0.74 |
| xxxx001 | xxxx | xxxx | ... | 0.23 |
| xxxx003 | xxxx | xxxx | ... | 0.11 |
| ⋮ | ⋮ | ⋮ | ⋮ | ⋮ |
| xxxxxxx | xxxx | xxxx | ... | ... |

FIG.11A

| PATIENT ID | PATIENT NAME | EXAMINATION DATE | ... | MALIGNANCY LEVEL |
|---|---|---|---|---|
| xxx0001 | xxxx | 1/23/2020 | ... | 0.28 |
| xxx0002 | xxxx | 1/23/2020 | ... | 0.87 |
| xxx0003 | xxxx | 1/23/2020 | ... | 0.72 |
| ⋮ | ⋮ | ⋮ | ⋮ | ⋮ |
| xxx1001 | xxxx | 2/1/2020 | ... | 0.10 |
| xxx1002 | xxxx | 2/1/2020 | ... | 0.21 |
| xxx1003 | xxxx | 2/1/2020 | ... | 0.67 |
| ⋮ | ⋮ | ⋮ | ⋮ | ⋮ |

FIG.11B

| | PATIENT ID | PATIENT NAME | EXAMINATION DATE | ... | MALIGNANCY LEVEL |
|---|---|---|---|---|---|
| G1 | xxx0002 | xxxx | 1/23/2020 | ... | 0.87 |
| | xxx0003 | xxxx | 1/23/2020 | ... | 0.72 |
| | xxx0001 | xxxx | 1/23/2020 | ... | 0.28 |
| | ⋮ | ⋮ | ⋮ | ⋮ | ⋮ |
| G2 | xxx1003 | xxxx | 2/1/2020 | ... | 0.67 |
| | xxx1002 | xxxx | 2/1/2020 | ... | 0.21 |
| | xxx1001 | xxxx | 2/1/2020 | ... | 0.10 |
| | ⋮ | ⋮ | ⋮ | ⋮ | ⋮ |

INFORMATION PROCESSING DEVICE AND MEDICAL IMAGE SYSTEM

CROSS-REFERENCE TO RELATED APPLICATIONS

The entire disclosure of Japanese Patent Application No. 2020-085921 filed on May 15, 2020 is incorporated herein by reference in its entirety.

BACKGROUND

Technological Field

The present invention relates to an information processing device and a medical image system.

Description of the Related Art

In recent years in the medical field, machine learning has been supporting imaging diagnosis, which used to be done by doctors. In machine learning, machines learn patterns and relations of a mass of data and performs identification, recognition, detection, prediction, and the like.

In clinical medicine, it is necessary to perform examinations and diagnoses appropriately and quickly, which requires efficiency improvement and optimization of examinations and diagnoses.

For example, there has been proposed a diagnosis support system to calculate scores of difficulty in diagnosis of patient cases and rank the cases for efficient diagnosis (see JP2017515574A). In this system, an appropriate doctor can be assigned to each case according to the diagnosis ability of doctors.

SUMMARY

In clinical medicine, further efficiency improvement and optimization of workflows are desired.

For example, in imaging of a patient, if additional imaging is required after a doctor interpreted an image(s) obtained by photographing the patient, it is necessary to ask the patient to come to the medical facility and take clothes off, as well as reserve the examination equipment, prepare and set up the photographing, which decreases the productivity.

In regard of information communication, timely contact with the medical workers is required because of necessity of immediate responses to patients with infectious diseases.

It is necessary that appropriate doctors (attribute, ability of image interpretation, etc.) deliver image interpretation in imaging diagnosis.

The present invention has been conceived in view of the problems in the conventional techniques as described above, and has an object of realizing efficiency improvement and optimization of workflows in medical fields.

To achieve at least one of the abovementioned objects, according to an aspect of the present invention, n information processing device reflecting one aspect of the present invention is interposed between an imaging control device and an image management device in communication, the information processing device including:
 an abnormality detector that performs detection of an abnormality in a medical image received from the imaging control device;
 a first hardware processor that determines, based on a result of the detection by the abnormality detector, content or a destination of transmission of the medical image or the result of the detection.

To achieve at least one of the abovementioned objects, according to another aspect of the present invention, a medical image system reflecting one aspect of the present invention including:
 the information processing device; and
 the image management device,
 wherein the image management device comprises:
  a storage that stores the plurality of medical images transmitted from the information processing device and priorities associated with the respective plurality of medical images; and
  a second hardware processor that determines an order of the plurality of medical images stored in the storage on a list to be displayed on a display based on the priorities associated with the plurality of medical images stored in the storage.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 6 shows an exemplary data configuration of a medical image database;

FIG. 10A shows exemplary data of medical images;

FIG. 10B shows exemplary display of the data sorted according to the malignancy level;

FIG. 11A shows exemplary data of medical images according to a modification; and FIG. 11B shows exemplary display of the data grouped by date of examination and sorted according to the malignancy level.

DETAILED DESCRIPTION OF THE EMBODIMENTS

Hereinafter, embodiments of an image processing device and a medical image system according to the present invention are described with reference to the drawings. However, the scope of the present invention is not limited to the embodiments or illustrated examples.

[Configuration of Medical Image System]

Figure 1:
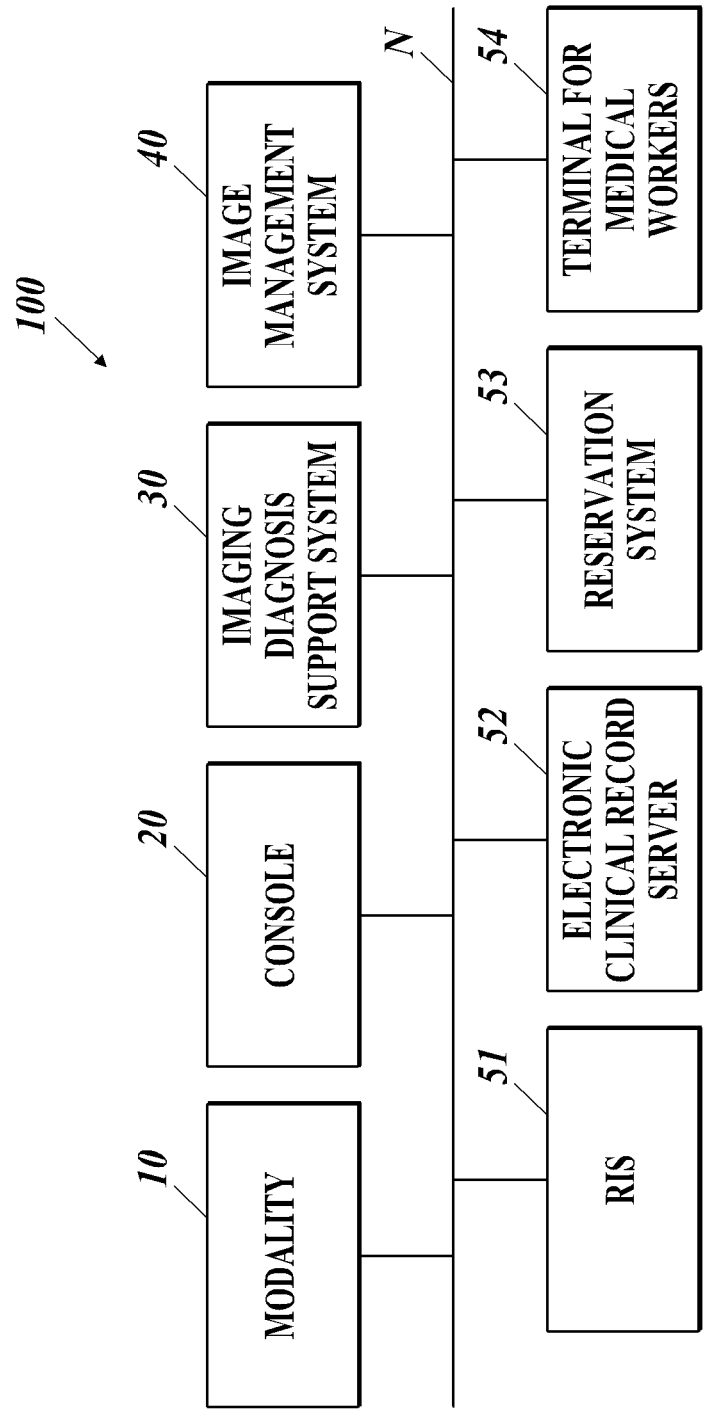
FIG. 1 shows a system configuration of a medical image system according to an embodiment of the present invention.

FIG. 1 shows a system configuration of a medical image system 100.

As shown in FIG. 1, the medical image system 100 includes a modality(s) 10, a console(s) 20, an imaging diagnosis support device 30, an image management device 40, an RIS (Radiology Information System) 51, an electronic clinical record server 52, a reservation system 53, and a terminal(s) for medical worker(s) 54, and is connected for data communication via a communication network N such as a LAN (Local Area Network). These components of the medical image system 100 are in conformity with HL7 (Health Level Seven), DICOM (Digital Image and Communications in Medicine) standard, or the like and communicate with one another in conformity with DICOM standard. The numbers of the modalities 10, the consoles 20, and the terminals for medical workers 54 are not particularly limited.

The modality 10 is an image generation device such as an X-ray imaging machine (DR, CR), an ultrasound diagnostic machine (US), a CT scanner and an MRI machine, and generates medical images by imaging the patients. The modality 10 writes attribute information (patient information, examination information, etc.) to headers of image files in conformity with DICOM standard, and thereby attaches the attribute information to the medical images.

The console 20 is an imaging control device that controls the imaging in the modality 10. The console 20 outputs imaging conditions and image reading conditions to the modality 10 and obtains the image data of the medical images imaged by the modality 10. The console 20 includes a controller, a display, an operation interface, a communication unit, and a storage and such components are connected by a bus.

The imaging diagnosis support device 30, which is an information processing device located in the communication network between the console 20 and the image management device 40, receives medical images from the console 20, and transmits the medical images to the image management device 40. The imaging diagnosis support device 30 uses artificial intelligence (AI) that performs imaging diagnosis and image analysis including detection of lesions of CAD (Computer Aided Diagnosis/Detection) on the medical images.

The image management device 40 stores and manages the image data of the medical images generated by the modality 10. The image management device 40 is, for example, PACS (Picture Archiving and Communication System).

The RIS 51 manages information in the radiology department such as examinations by the radiation devices, reservations of treatments, results of examinations, and the like. The RIS 51 manages examination orders issued by the electronic clinical record server 52 and transmits the examination orders to the modality 10 used in the examinations.

The electronic medical clinical server 52 generates electronic clinical record information including treatments and diagnoses to patients and examination orders for requesting the examinations of the patients according to the operation input via the terminal for medical workers 54.

The reservation system 53 manages reservations of the examinations such as imaging examinations using the modality 10, for example, in the medical facility.

The terminal for medical workers 54 is a computer device such as a personal computer (PC) used by medical workers. The medical workers creates the electronic clinical records, generates the examination orders, views the medical images, and create image interpretation reports on the terminals for medical workers 54. The terminal for medical workers 54 includes a controller, a display, an operation interface, a communication unit, and a storage, and such components are connected by a bus.

[Configuration of Imaging Diagnosis Support Device]

Figures 2, 3:
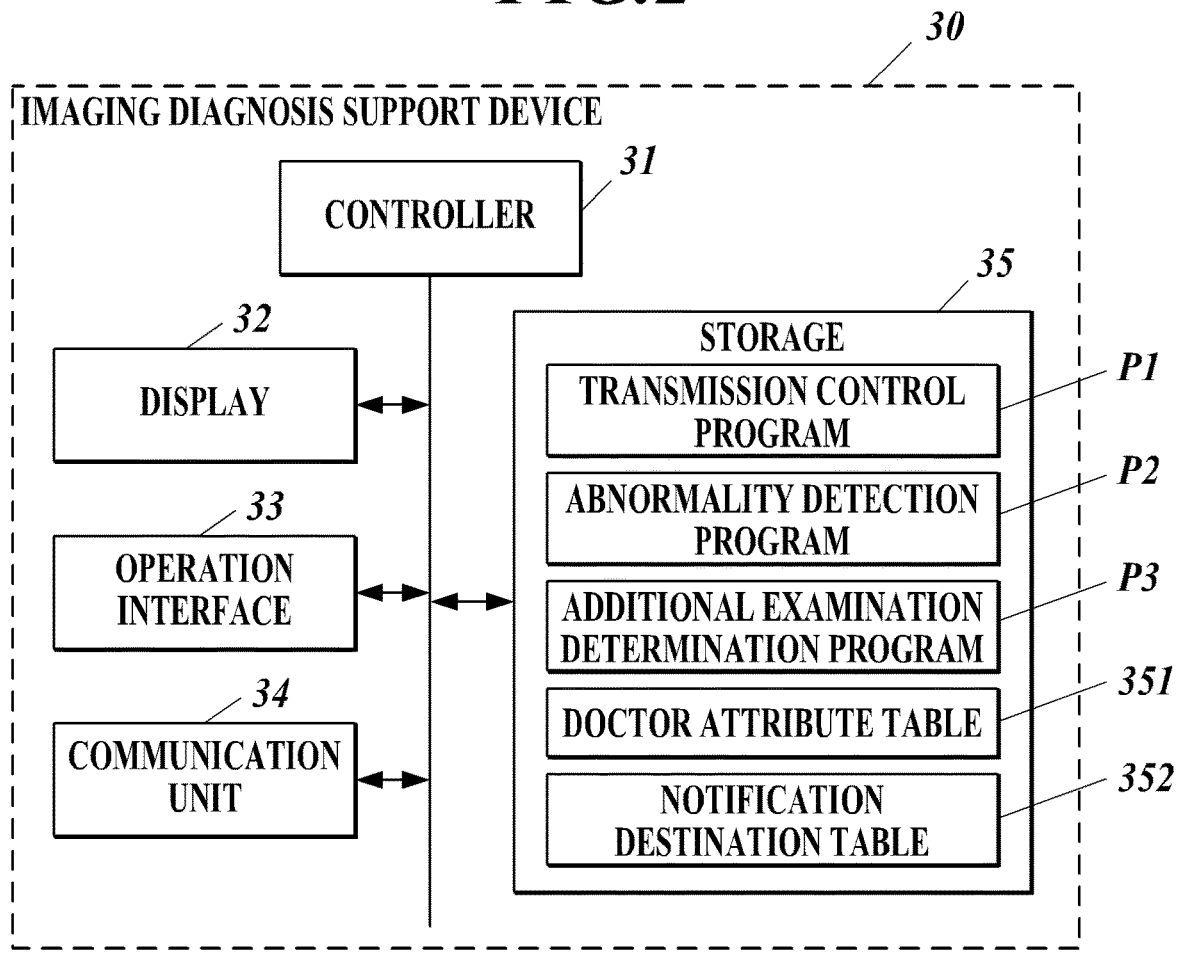
FIG. 2 is a block diagram showing a functional configuration of an imaging diagnosis support device.
FIG. 3 shows an exemplary data configuration of a doctor attribute table.

FIG. 2 shows a functional configuration of the imaging diagnosis support device 30.

As shown in FIG. 2, the imaging diagnosis support device 30 includes a controller (first hardware processor) 31, a display 32, an operation interface 33, a communication unit 34, and a storage 35, and such components are connected by a bus.

The controller 31, which includes a central processing unit (CPU), a random access memory (RAM), and the like, centrally controls processing operations of the components of the imaging diagnosis support device 30. Specifically, the CPU retrieves various processing programs stored in the program storage 35, deploys them in the RAM, and executes various kinds of processing in cooperation with the programs.

The display 32, which includes a monitor of a liquid crystal display (LCD), shows various screens according to the display signals input by the controller 31.

The operation interface 33, which includes a keyboard with cursor keys, letter and number input keys, various function keys, and the like, and a pointing device such as a mouse, outputs key operations on the keyboard, operation signals input by the mouse operation, or the like to the controller 31.

The communication unit 34, which includes a network interface, transmits and receives data to and from an external device(s) connected via the communication network. For example, the communication unit 34 receives the medical images obtained by imaging of the patients by the modality 10 from the console 20. The communication unit 34 transmits the medical images to the image management device 40.

The storage 35 is a memory device including a hard disk drive (HDD) and a non-volatile memory. The storage 35 stores various programs executed by the controller 31 and parameters and data required for executing the programs. For example, the storage 35 stores a transmission control program P1, an abnormality detection program P2, and an additional examination determination program P3. The storage 35 also stores the doctor attribute table 351, and a notification destination table 352.

The transmission control program P1 is a program for executing a process of determination of contents to be sent or a recipient of a medical image(s) or an abnormality detection result based on a medical image or an abnormality detection result.

The abnormality detection program P2 is a program for executing a process of detection of an abnormality from the medical image.

The additional examination determination program P3 is a program for executing a process of determination whether an additional examination (additional imaging, reimaging) is required.

The doctor attribute table 351 is a table for managing the attribute information of doctors. The attribute information may be input from the imaging diagnosis support device 30 or any device that is connectable to the imaging diagnosis support device 30. FIG. 3 shows an exemplary data configuration of the doctor attribute table 351. A doctor name, user ID, specialty, image interpretation ability, fatigue level, and availability for each of the doctors are stored in the doctor attribute table 351.

The doctor name is a name of a doctor.

The user ID is a user ID for the doctor using the medical image system 100.

The specialty is a medical department which the doctor is specialized in or belongs to.

The image interpretation ability is information indicating the level of the image interpretation skill of the doctor. The image interpretation ability is, for example, represented by classification of high, medium, and low, which is determined by the years of experience, the cumulative number of the interpreted images, and the like.

The fatigue level is information indicating the degree of fatigue of the doctor. The fatigue level is, for example, represented by classification of high, medium, ad low, which is determined by the number of the interpreted images in a predetermined period. The fatigue level is determined by the number of the interpreted images on a day in the simplest way. The doctor (user) her/himself can set the fatigue level.

The availability is information indicating the availability of the doctor (0-100%, etc.). The availability is calculated from the number of images to be interpreted, the reservations, the current image interpretation status, and the like. The doctor (user) her/himself can set the availability (especially in a remote site of image interpretation).

The notification destination table 352 is a table for managing a destination of notification from the imaging diagnosis device 30 for each of the medical workers (users). A user ID, a name, an e-mail address, and the like associated with each other are stored in the notification destination table 352.

The user ID, name, and e-mail address are each the medical worker's. Other destination information may be stored instead of the e-mail address.

The controller 31 detects an abnormality in the medical image received from the console 20 in association with the abnormality detection program P2. That is, the controller 31 functions as an abnormality detector.

The controller 31 generates a lesion name (disease name), a position of the lesion, a size of the lesion, a category of the lesion, a malignancy level, or a malignancy level map.

The category of the lesion is information indicating the degree of suspicion of malignancy. In mammography, a lesion is divided into five categories as shown below. Categories 3 to 5 require detailed examination.

Category 1: no abnormality
Category 2: clearly benign
Category 3: benign (But cannot deny malignancy)
Category 4: suspected of malignancy (There is high possibility of malignancy, but there is still possibility of benignity. Cytology and biopsy are recommended.)
Category 5: malignant (Breast cancer is almost certain)

The malignancy level is a numerical measure of the level of malignancy based on a name, position, size, category and the like of the lesion. The malignancy level may be calculated for each medical image. Alternatively, the malignancy level may be calculated for each lesion on one medical image (ex. lung cancer: 0.13, tuberculosis: 0.72, aerothorax: 0.86, etc.).

Figure 4A:
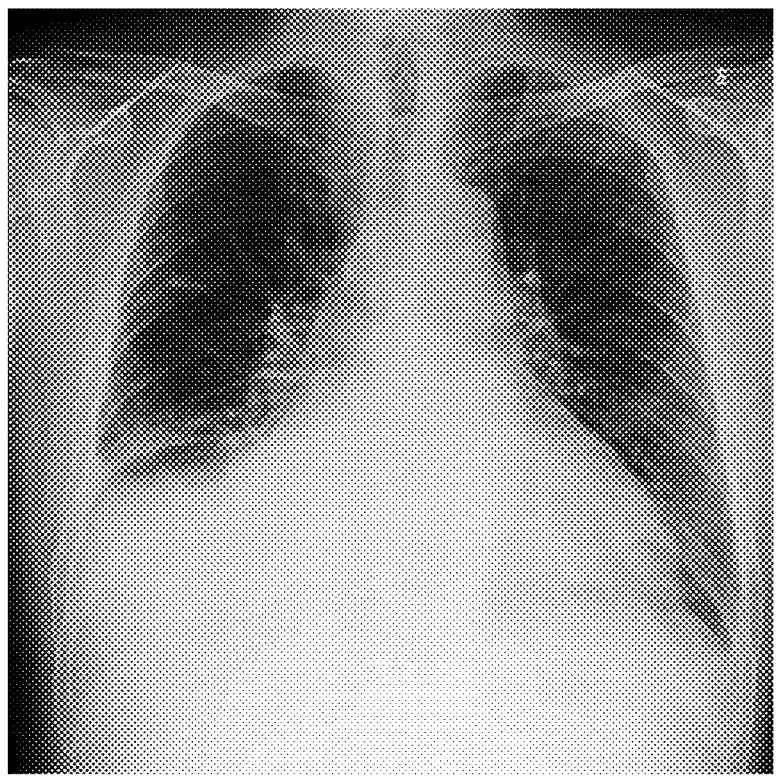
FIG. 4A is an example of a chest X-ray image.
Figure 4B:
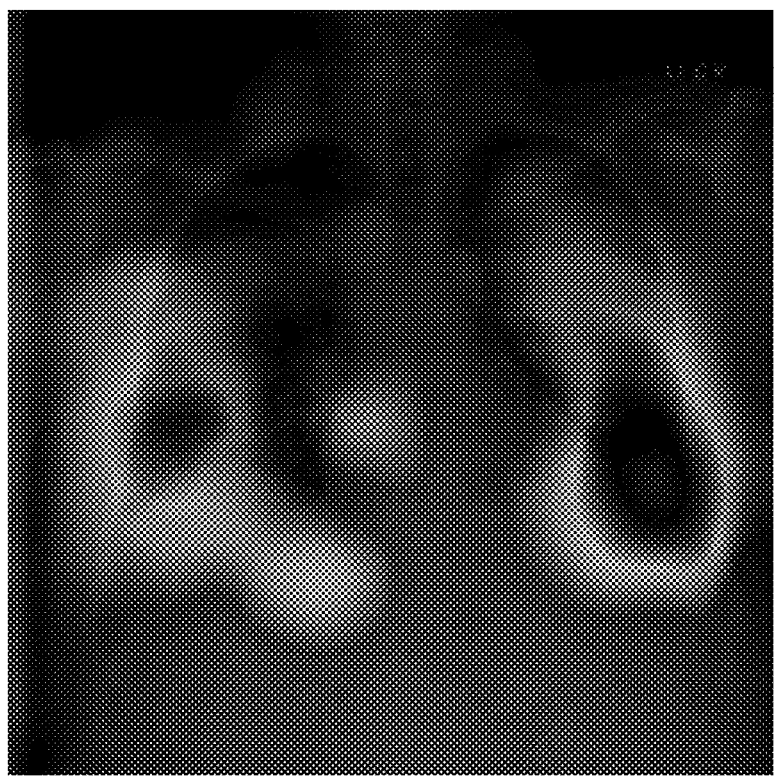
FIG. 4B is an example of a malignancy level map generated for the chest X-ray image.

The malignancy level map is a heatmap colored according to the malignancy level of each area on the medical image. The contrasting malignancy levels (numerical data) are visualized in the malignancy level map. An exemplary malignancy level map of a chest X-ray image in FIG. 4A is shown in FIG. 4B. It is desirable that a region with a high malignancy level is represented by red, for example, to draw attention to the region with a high malignancy level.

The controller 31 writes a "SOP instance UID" of the medical image for which the malignancy level map is created on a tag "reference SOP instance UID" of the malignancy level map, and thereby records which malignancy level map corresponds to which medical image.

The feature of analysis including abnormality detection is realized by machine learning. The controller 31 outputs an abnormality detection result such as possible diseases using a detector that have learned pre-prepared data set (combinations of medical images and abnormality detection results in the concerning medical images).

The controller 31 presents whether an additional examination or re-imaging is required and what item is to be examined in cooperation with the additional examination determination program P3. That is, the controller 31 functions as an additional examination determining means. The examination items (what item is to be examined) are information specifying examination details (modality, region to be imaged, etc.). Specifically, the controller 31 presents at least one of the modality 10, the region to be imaged, and the imaging method. The imaging method includes specifying a direction of imaging, enlargement, and the like.

The controller 31 determines information to be transmitted or a recipient of the medical image or the detection result based on the abnormality detection result in cooperation with the transmission control program P1. In this embodiment, the recipient includes not only the actual recipient of the medical image or the detection result but also a publication range which the medical image or the detection result is open to.

For example, the controller 31 determines whether the medical image is transmitted to the image management device 40 based on the detection result.

The controller 31 determines a device to which the medical image or the detection result is transmitted based on the detection result. The device to which the medical image or the detection result is transmitted includes the image management device 40 (PACS), the console 20, the RIS 51, the electronic clinical record server 52, the reservation system 53, the terminal for medical workers 54 (including a tablet terminal and a mobile terminal), and the HIS (Hospital Information System).

The controller 31 determines a medical worker who is requested to interpret the medical image(s) based on the detection result and the attributes of the medical workers. The attributes of the medical workers include at least one of the specialty, the image interpretation ability, the fatigue level, and the availability.

The controller 31 assigns a priority for displaying the medical image to the medical image based on the detection result, and transmits the priority associated with the medical image to the image management device 40.

The controller 31 updates the fatigue level and the availability in the doctor attribute table 351 stored in the storage 35 based on the information on the doctors obtained from the image management device 40, the terminal for medical workers 54, and the like. The timing for update may be every 10 minutes, every hour, or any other time.

[Configuration of Image Management Device]

Figure 5:
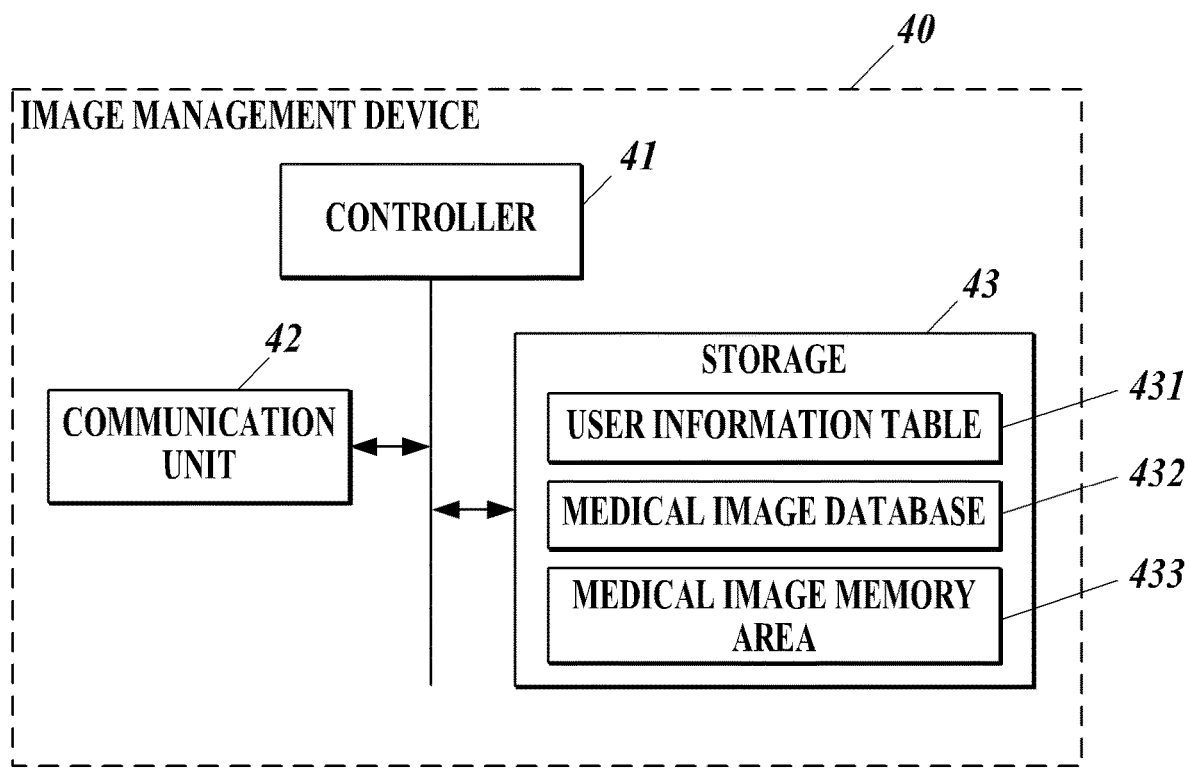
FIG. 5 is a block diagram showing a functional configuration of the image management device.

FIG. 5 shows a functional configuration of the image management device 40.

As shown in FIG. 5, the image management device 40 includes a controller (second hardware processor) 41, a communication unit 42, and a storage 43, and such components are connected by a bus.

The controller 41, which includes a CPU and a RAM, centrally controls processing operations of the components of the image management device 40. The CPU retrieves various processing programs stored in the program storage 43, deploys them in the RAM, and executes various kinds of processing in cooperation with the programs.

The communication unit 42, which includes a network interface, transmits and receives data to and from an external device(s) connected via the communication network N.

The storage 43 is a memory device including an HDD and a non-volatile memory. The storage 43 stores various programs executed by the controller 41 and parameters and data necessary for executing the programs. For example, the storage 43 stores a user information table 431 and a medical image database 432. The storage 43 includes a medical image memory area 433.

The user information table 431 is a table for managing the information on users (medical workers) using the medical image system 100 by each. The user information table 431 stores a user ID, name, facility, specialty, and the like associated with each other for each user.

The user ID is user identification information, and the name is a name of the user.

The facility is a medical facility to which the user belongs.

The specialty is a medical department which the user is specialized in.

The medical image database 432 is a database for managing information on the medical images managed in the image management device 40. FIG. 6 shows an exemplary data configuration of the medical image database 432. A patient ID, a patient name, examination date and time, an examination ID, a modality, a SOP instance UID, an image file name, a file storage location, an abnormality detection result, an image interpretation doctor, a priority, and the like are associated with each other in the medical image database 432.

The patient ID and the name is a patient ID and a name of the patient who undergoes an imaging examination.

The examination date and time is date and time when the examination concerning the medical image.

The examination ID is identification information of the examination concerning the medical image.

The modality is a modality used in the examination (imaging)

The SOP instance UID is identification information allotted to the medical image.

The image file name is a name of the file containing the medical image.

The file storage location is information indicating a destination of the file of the medical image in the medical image memory area 433.

The abnormal detection result, which is information obtained by the abnormality detection process for the medical image, includes presence/absence of an abnormality, a name of a lesion, a position of the lesion, a size of the lesion, a category of the lesion, and a malignancy level.

The image interpretation doctor is a doctor who is assigned to interpret the medical image. Specifically, the information on the image interpretation doctor determined in an image interpretation doctor assignment process described later (refer to FIG. 9) is obtained from the imaging diagnosis support device 30 and stored in the field "image interpretation doctor."

The priority is a priority for displaying the medical image. In this embodiment, the malignancy level deduced from the medical image is used as the priority.

The medical image memory area 433 stores the files of the medical images.

As the image file name and location of the medical image are associated with the priority in the medical image database 432, the medical image transmitted from the imaging diagnosis support device 30 and associated with the priority is stored in the storage 43.

In response to a request of acquisition of the medical image from an external device via the communication unit 42, the controller 41 transmits display data for displaying the requested medical image to the external device according to the acquisition request.

The controller 41 determines an order of displaying a list of medical images on a display means (the display of the terminal for medical workers 54, or the like) based on the priorities associated with the medical images and stored in the storage 43. That is, the controller 41 functions as a display control means.

[Operation of Imaging Diagnosis Support Device]

Next, operation of the imaging diagnosis support device 30 is described.

Figure 7:
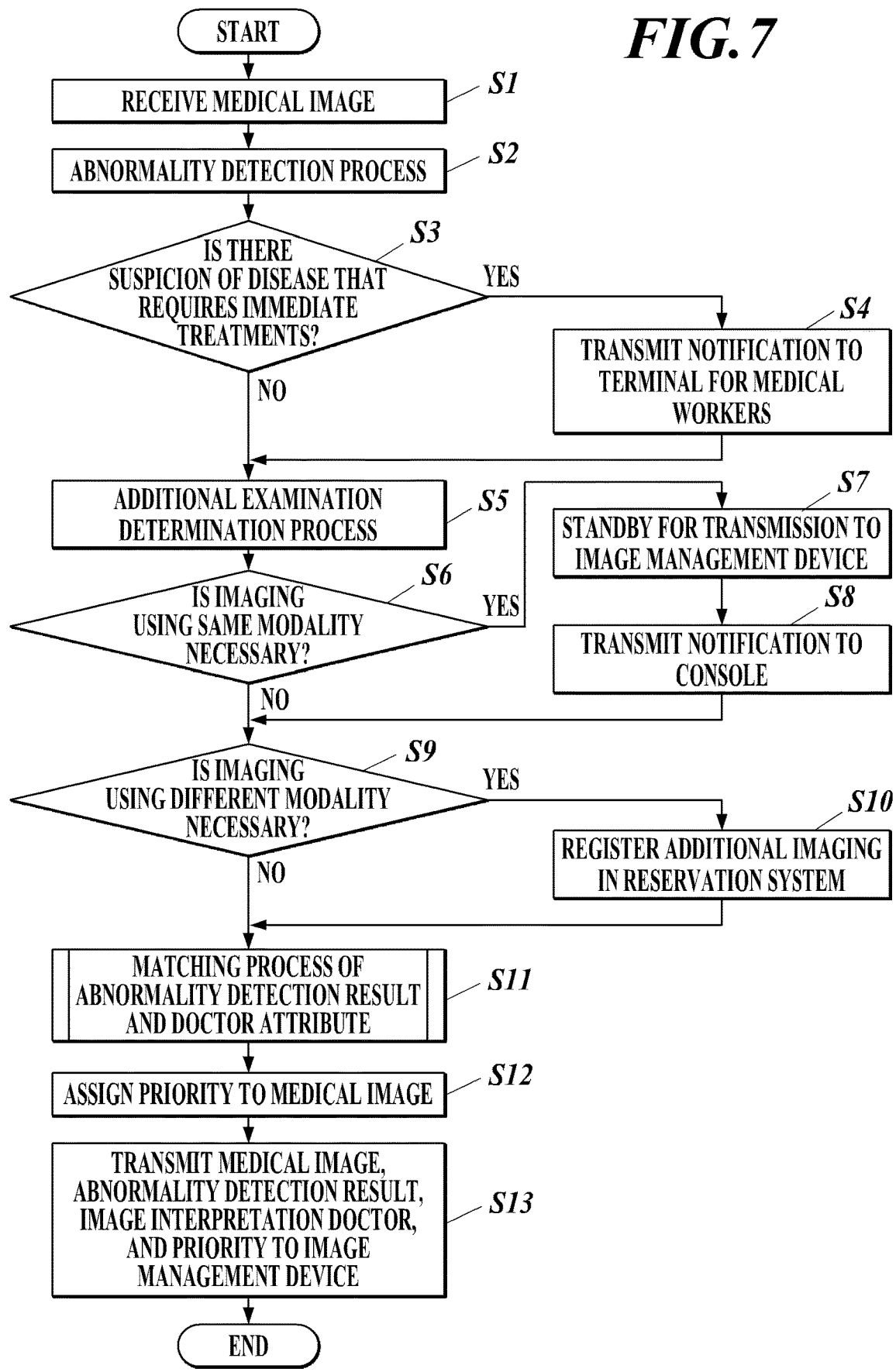
FIG. 7 is a flowchart showing an imaging diagnosis support process executed by the image diagnosis support device.

FIG. 7 is a flowchart showing an imaging diagnosis support process executed by the imaging diagnosis support device 30. This process is executed by software processing by the CPU of the controller 31 in association with the programs stored in the storage 35 (the transmission control program P1, the abnormality detection program P2, the additional examination determination program P3).

First, the controller 31 receives a medical image generated by the modality 10 from the console 20 via the communication unit 34 (Step S1).

Next, the controller 31 executes an abnormality detection process on the medical image using the detector obtained by machine learning (Step S2). The controller 31 detects an abnormality (possible lesion, image error, etc.), and generates data on the name of the lesion, the position of the lesion, the size of the lesion, the category of the lesion, and the malignancy level. A technique involving deep learning may be employed in the abnormality detection on the medical image.

Techniques concerning a lesion detection task on a chest X-ray image using deep learning are disclosed in the following documents, for example.

Wang, X. et al. ChestX-ray8: hospital-scale chest X-ray database and benchmarks on weakly-supervised classification and localization of common thorax diseases. Preprint at https://arxiv.org/abs/1705.02315 (2017).

Baltruschat, I. M. et al. Comparison of Deep Learning Approaches for Multi-Label Chest X-Ray Classification. Preprint at https://arxiv.org/abs/1803.02315 (2018).

Here, the controller 31 determines whether there is a suspicion of a disease which requires immediate treatments such as an infectious disease based on the detection result (Step S3). For example, the controller 31 determines whether there is a suspicion of tuberculosis, pneumonia, and the like, in the case of chest disease.

If it is determined that there is a suspicion of a disease requiring immediate treatments (Step S3; YES), the controller 31 notifies the terminal for medical workers 54 possessed by a doctor or technician who requested the examination concerning the medical image via the communication unit 34 (Step S4).

The doctor, technician, or the like who requested the examination concerning the medical image is attached to the medical image as attribute information, for example. The controller 31 reads out a notification destination such as an e-mail address of the doctor, technician, or medical worker who requested the examination concerning the medical image from the notification destination table 352 in the storage 35, and transmits a notification about a suspicion of a disease requiring immediate treatments to the destination.

The controller 31 may display a pop-up window with a message that there is a suspicion of a disease requiring immediate treatments on the display of the terminal for medical workers 54 or the console 20. In the case where a list of examinations is displayed on the display of the terminal for medical workers 54 or the console 20, the controller 31 may display a mark indicating that there is a suspicion of a disease requiring immediate treatments in a row of the concerning examination on the list. The controller 31 may displays a blinking icon dedicated for showing that there is a suspicion of a disease requiring immediate treatments on the display of the terminal for medical workers 54 or the console 20.

If it is determined that there is no suspicion of a disease requiring immediate treatments at Step S3 (S3; NO), or after Step S4, the controller 31 performs an additional examination determination process (Step S5). In the additional examination determination process, the controller 31 determines whether an additional examination is required or not. The controller 31 determines the modality 10 to be used in the additional examination, the region to be imaged, the imaging method, and the like.

For example, the controller 31 determines that re-imaging is required for an image that does not have an image quality above a predetermined level due to body movement or foreign matter inclusion or an image that is not suitable for diagnosis such as a chest image lacking a lung region. In a chest image lacking a lung region, the entire thorax is not in the irradiated area, and the lung region is missing. The controller 31 determines a direction of imaging, an enlargement, and the like that are required in additional imaging based on the abnormality detection result.

Here, the controller 31 determines whether imaging (re-imaging, additional imaging) using the same modality 10 as the one which generated the medical image received at Step S1 is required or not (Step S6).

If imaging using the same modality 10 is required (Step S6; YES), the controller 31 is on standby for transmission of the medical image received at Step S1 to the image management device 40 (Step S7), and notifies via the communication unit 34 the console 20 which transmitted the concerning medical image that re-imaging or additional imaging is required and of an order of re-imaging or additional imaging (item to be examined, region to be imaged, direction of imaging, etc.) (Step S8).

The order of the re-imaging or additional imaging is displayed on the display of the console 20. For example, the controller 31 displays a pop-up window showing the order of the re-imaging or additional imaging on the display of the console 20. In the case where a list of examinations is displayed on the display of the console 20, the controller 31 may display a mark indicating re-imaging or additional imaging in a row of the concerning examination on the list. The controller 31 may display a blinking icon indicating re-imaging or additional imaging on the display of the console 20.

In the case of the re-imaging using the same modality 10, after the steps from Step S1 are performed on the medical image generated by the re-imaging, the medical image in the re-imaging is to be transmitted unless further re-imaging is required. The medical image previously imaged is not transmitted to the image management device 40.

If imaging using the same modality is not required at Step S6 (Step S6; NO), or after Step S8, the controller 31 determines whether imaging using the modality 10 different than the one which generated the medical image received at Step S1 is required as a result of the additional examination determination process (Step S9).

If imaging using a different modality 10 is required (Step S9; YES), the controller 31 registers additional imaging to the reservation system 53 (Step S10). Specifically, the controller 31 transmits information on the modality 10 to be used in the additional imaging, the region to be imaged, the imaging method, and the like to the reservation system 53 via the communication unit 34. An examination reservation concerning the additional imaging is registered in the reservation system 53.

The controller 31 may transmit an order of the additional imaging to the reservation system 53 after displaying on the display 32 that the additional imaging is required and what are the modality to be used in the additional imaging, the region to be imaged, the imaging method, and the like, and then waiting for the user to transmit an order via the operation interface 33 before the additional imaging is registered to the reservation system 53.

If imaging using a different modality 10 is not required at Step S9 (Step S9; NO), or after Step S10, the controller 31 performs a matching process of the abnormality detection result and the attribute of the doctor (Step S11).

The matching process of the abnormality detection result and the attribute of the doctor is described below with reference to FIG. 8.

The controller 31 obtains the abnormality detection result (name of the lesion, position of the lesion, size of the lesion, category of the lesion, malignancy level, etc.) obtained in the abnormality detection process at Step S2 (Step S21).

Next, the controller 31 determines difficulty of diagnosis for the medical image (Step S22). For example, the controller 31 sets "difficulty: high" for a case of a disease which is difficult to diagnose based on the malignancy level included in the abnormality detection result. Specifically, the controller 31 sets "difficulty: high" for the malignancy level of 0.4 to 0.6, "difficulty: medium" for the malignancy level of 0.2 to 0.4 or 0.6 to 0.8, "difficulty: low" for the malignancy level of 0 to 0.2 or 0.8 to 1.0. According to the criteria for determination used here, it is most difficult to diagnose a disease by the medical image with a result indicating a medium malignancy level.

The difficulty may be calculated from the name, position, and size of the lesion. In determination by the name of the lesion, the less common the lesion, the higher the difficulty. In determination by the position of the lesion, the more structures overlap at the position, the higher the difficulty. In determination by the size of the lesion, the smaller the size, the higher the difficulty.

Next, the controller 31 obtains the attribute information of each doctor (specialty, image interpretation ability, fatigue level, availability) from the doctor attribute table 351 stored in the storage 35 (Step S23).

Next, the controller 31 determines the specialty appropriate for the lesion from the name of the lesion included in the abnormality detection result (Step S24).

Next, the controller 31 picks up interpretation doctor options (option group A) based on the specialty (Step S25). Specifically, the controller 31 extracts the doctors with the attribute information including the "specialty" matching with the one determined at Step S24.

Next, the controller 31 picks up interpretation doctor options (option group B) based on the difficulty of the medical image and the image interpretation ability of the doctor from the option group A (Step S26). Specifically, the controller 31 extracts doctors in the option group A with the attribute information including the "image interpretation ability" corresponding to the difficulty determined at Step S22. For example, doctors with "interpretation ability: high" are picked up for "difficulty: high," and doctors with "interpretation ability: low" are picked up for "difficulty: low."

Next, the controller 31 performs the image interpretation doctor assignment process (Step S27). In the image interpretation doctor assignment process, the image interpretation doctor is assigned based on the fatigue level and the availability included in the attribute information of the doctor.

Figure 9:
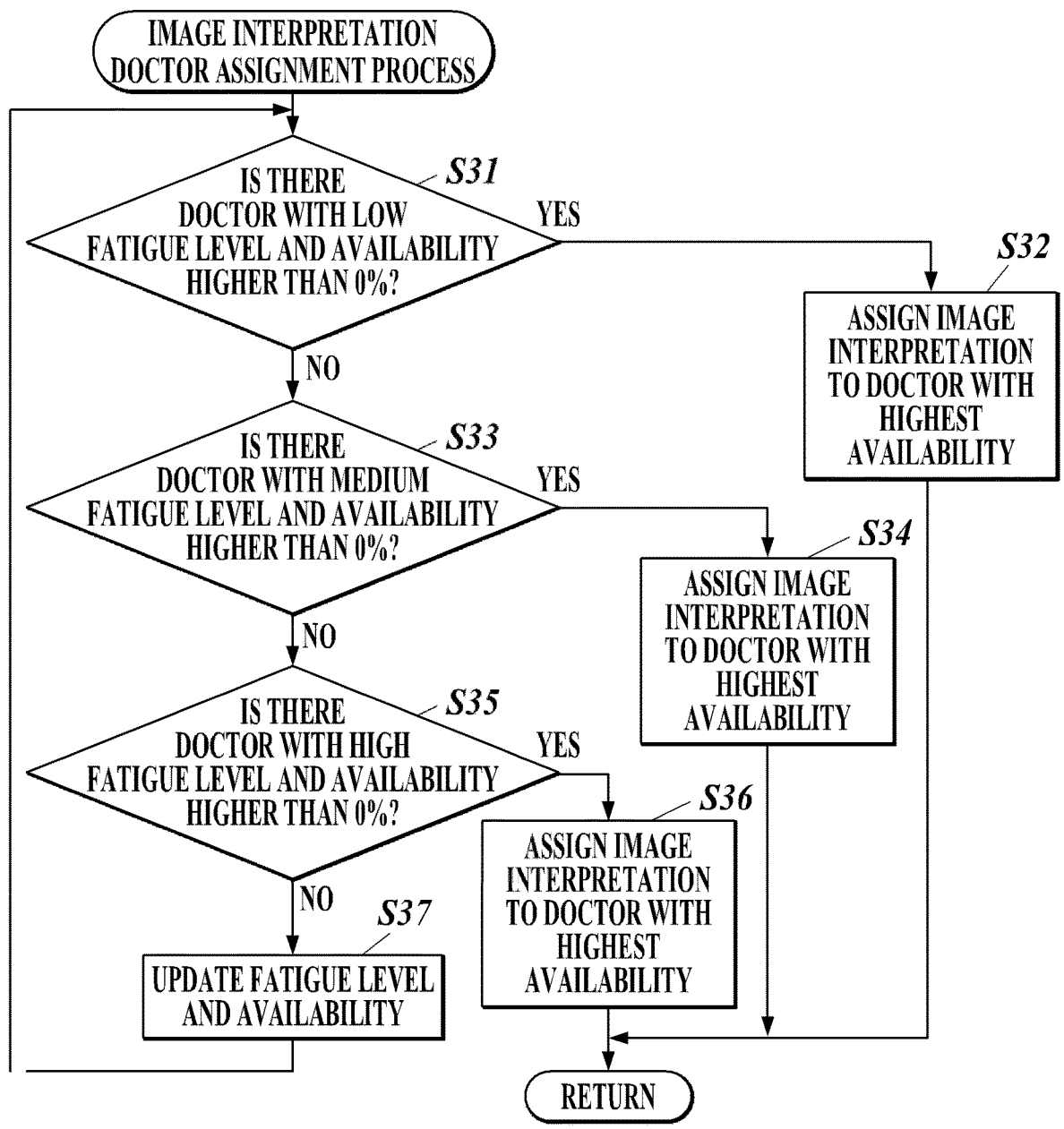
FIG. 9 is a flowchart showing an image interpretation doctor assignment process.

The image interpretation doctor assignment process is described with reference to FIG. 9.

The controller 31 determines whether there is a doctor with a low fatigue level and availability higher than 0% among the doctors included in the option group B (Step S31).

If there is a doctor with a low fatigue level and availability higher than 0% among the doctors included in the option group B (Step S31; YES), the controller 31 assigns a doctor with the highest availability among the doctors with a low fatigue level and availability higher than 0% (Step S32).

If there is no doctor with a low fatigue level and availability higher than 0% among the doctors included in the option group B at Step S31 (Step S31; NO), the controller 31 determines whether there is a doctor with a medium fatigue level and availability higher than 0% among the doctors included in the option group B (Step S33).

If there is a doctor with a medium fatigue level and availability higher than 0% among the doctors included in the option group B (Step S33; YES), the controller 31 assigns a doctor with the highest availability among the doctors with a medium fatigue level and availability higher than 0% (Step S34).

If there is no doctor with a medium fatigue level and availability higher than 0% among the doctors included in the option group B at Step S3 (Step S33; NO), the controller 31 determines whether there is a doctor with a high fatigue level and availability higher than 0% among the doctors included in the option group B (Step S35).

If there is a doctor with a high fatigue level and availability higher than 0% among the doctors included in the option group B (Step S35; YES), the controller 31 assigns a doctor with the highest availability among the doctors with a high fatigue level and availability higher than 0% (Step S36).

If there is no doctor with a high fatigue level and availability higher than 0% among the doctors included in the option group B at Step S35 (Step S35; NO), the controller 31 obtains the fatigue level and availability of each doctor and updates the fatigue level and availability of each doctor in the doctor attribute table 351 in the storage 35 (Step S37).

The controller 31 returns to Step S31 after Step S37 and repeats the steps based on the updated fatigue level and availability.

The controller 31 ends the image interpretation doctor assignment process after Step S32, S34, or S36.

Figure 8:
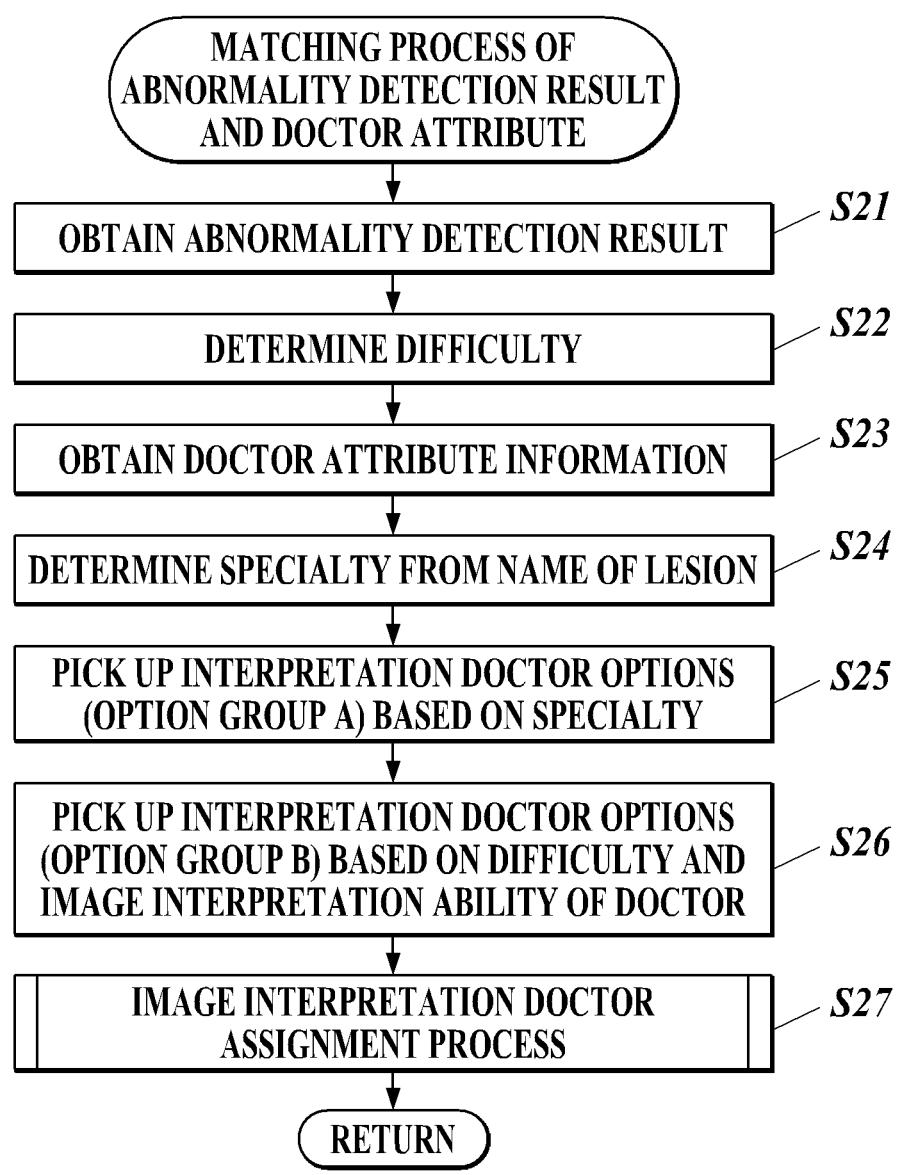
FIG. 8 is a flowchart showing a matching process of an abnormality detection result and an attribute of a doctor.

After the image interpretation doctor assignment process, the controller 31 ends the matching process of the abnormality detection result and the attribute of the doctor in FIG. 8.

After Step S11, the controller 31 assigns a priority for displaying the medical image to the medical image based on the abnormality detection result (Step S12) in FIG. 7. Here, the controller 31 uses the "malignancy level" as the priority.

Next, the controller 31 associates the medical image with the abnormality detection result (presence/absence of abnormality, name of the lesion, position of the lesion, size of the lesion, category of the lesion, and malignancy level), the image interpretation doctor, and the priority with each other, and transmits them to the image management device 40 via the communication unit 34 (Step S13).

In the case where the malignancy level map is generated in the abnormality detection process, the controller 31 transmits the malignancy level map with the medical image to the image management device 40 via the communication unit 34.

The imaging diagnosis support process is ended here.

The controller 41 of the image management device 40 receives the medical image, the abnormality detection result, the image interpretation doctor, and the priority which are transmitted from the imaging diagnosis support device 30 via the communication unit 42. The controller 41 stores the medical image transmitted from the imaging diagnosis support device 30 in the medical image memory area 433 of the storage 43 and stores the information on the medical image in the medical image database 432. The controller 41 stores, in the medical image database 432, a patient ID, a patient name, examination date and time, an examination ID, a modality, a SOP instance UID, an image file name, a file storage location, an abnormality detection result, an image interpretation doctor, a priority, and the like associated with each other.

The patient ID, patient name, examination date and time, examination ID, modality, and SOP instance UID are obtained from the attribute information of the medical image.

In the case where the controller 41 receives the malignancy level map with the medical image from the imaging diagnosis support device 30, the controller 41 stores in the storage 43 the malignancy level map associated with the medical image for which the map is created. Specifically, the controller 41 writes the "SOP instance UID" of the medical image for which the malignancy level map is created on a tag "reference SOP instance UID" of the malignancy level map, and thereby associates the malignancy level map with the medical image.

When the terminal for medical workers 54 is accessed, the controller 41 specifies the medical worker who is operating the terminal for medical workers by the "user ID" input in the terminal for medical workers 54. Specifically, the controller 41 refers to the user information table 431 in the storage 43 and specifies the medical worker (name of user) who is operating the terminal for medical workers 54 based on the user ID.

The controller 41 refers to the medial image database 432 in the storage 43, extracts records (medical images) which are associated with the medical worker who is operating the terminal for medical workers 54 in the "image interpretation doctor" field, and displays a list (examination list) of medical images to be interpreted by the medical worker who is operating the terminal for medical workers 54 on the display of the terminal for medical workers 54.

FIG. 10A shows exemplary data (patient ID, patient name, examination date, malignancy, etc.) dedicated to the medical images which the medical worker who is operating the terminal for medical workers 54 is requested to interpret.

FIG. 10B shows exemplary display of the data in FIG. 10A sorted according to the malignancy level (priority). In FIG. 10B, the data (patient ID, patient name, examination date, malignancy, etc.) associated with each of the medical images is sorted in order of malignancy from high to low.

The controller 41 displays the medical image selected on the list on the display of the terminal for medical workers 54 according to an operation via the operation interface of the terminal for medical workers 54.

The controller 41 may display the malignancy level map associated with the medical image on the display along with the medical image when displaying the medical image for interpretation.

As described hereinbefore, the imaging diagnosis support device 30 according to this embodiment determines contents and a destination of transmission of the medical image or the detection result based on the result of the detection of an abnormality. Thus, efficiency improvement and optimization of workflows in medical fields may be realized.

For example, in the case where there is a suspicion of a disease which requires immediate treatments such as an infectious disease, the medical workers such as a doctor who requested the examination or a technician are notified of that via the terminal for medical workers 54, based on the detection result. In this way, timely communication with the medical workers is possible.

The imaging diagnosis support device 30 determines the medical worker who is to be requested to interpret the medical image based on the detection result and the attributes of the medical worker, and then determines thereby the publication range which the medical image or the detection result is open to. This makes it possible to request an appropriate medical worker to interpret the medical image.

The imaging diagnosis support device 30 determines whether to transmit the medical image to the image management device 40 based on the detection result. For example, in the case where re-imaging using the same modality 10 is required, the medical image taken previously is not transmitted to the image management device 40.

It is not convenient for the doctor, technician, or patient if additional imaging is to be requested after the doctor interprets the medial image. As additional imaging is determined by analysis of the medical image right after the imaging, the additional imaging may be requested while the patient is in the imaging room, which improves productivity.

The imaging diagnosis support device 30 transmits a request for re-imaging or additional imaging to the console 20 in the case where the re-imaging or additional imaging using the same modality 10 is required.

The image diagnosis support device 30 transmits information on the modality 10 used in the additional imaging, the region to be imaged, the imaging method, and the like to the reservation system 53 in the case where imaging using a different modality 10 is required based on the detection result.

The imaging diagnosis support device 30 may transmit the priority for displaying the medical image associated with the medical image to the image management device 40, presenting the priority of the medical image to the image management device 40.

The image management device 40 determines the order of the medical images on the list to be displayed on the terminal for medical workers 54 based on the priority associated with each of the medical images.

[Modification]

In a modification, in the case where the medical images to be interpreted on the list are associated with different dates of examination, the medical images on different dates are not mixed up.

The controller 41 of the image management device 40 determines an order of the medical images for displaying the list on the display (the display of the terminal for medical workers 54, etc.) based on the priority of each of the medical images stored in the storage 43.

The controller 41 displays the list of the medical images grouped by a predetermined period according to the examination date of each of the medical images included in the list, and determines an order of the medical images in the predetermined period based on the priority of each of the medical images. In the modification, a day (0 o'clock to 24 o'clock on the same day) is the predetermined period.

When the terminal for medical workers is accessed, the controller 41 specifies the medical worker who is operating the terminal for medical workers by the "user ID" input in the terminal for medical workers 54.

The controller 41 refers to the medial image database 432 in the storage 43, extracts records (medical images) which are associated, in the "image interpretation doctor" field, with the medical worker who is operating the terminal for medical workers 54, and displays a list (examination list) of the medical images to be interpreted by the medical worker who is operating the terminal for medical workers 54 on the display of the terminal for medical workers 54.

FIG. 11A shows exemplary data (patient ID, patient name, examination date and time, malignancy, etc.) dedicated to the medical images which the medical worker who is operating the terminal for medical workers 54 is requested to interpret. In the modification, the malignancy level deduced from the medical image is used also as the priority.

FIG. 11B shows exemplary display of the data in FIG. 11A grouped by examination date and sorted according to the malignancy level (priority). In FIG. 11, the data (patient ID, patient name, examination date, malignancy, etc.) corresponding to each of the medical images are grouped into Group G1 and G2 by examination date. The data corresponding to the medical images with the examination date of "Jan. 23, 2020" are sorted by malignancy from high to low in Group G1. The data corresponding to the medical images with the examination date of "Feb. 1, 2020" are sorted by malignancy from high to low in Group G2.

As described above, when the list of the medical images generated on multiple examination dates is displayed, the data on the same date are sorted and the medical images on different dates are not mixed up. That is, the medical images with high malignancy are displayed on the top of the list among the medical images on the same date.

When the order of the medical images on the list is determined according to the priority only, interpretation of a medical image with low priority may be put back. In the modification, however, a medical image is not replaced with another in a different group of the "predetermined period". This makes it possible not to unnecessarily put back interpretation of a medical image with low priority.

The "predetermined period" for grouping the examination dates and times are not limited to one day. The examination dates and times may be grouped by multiple days, by two or three days for example.

The above embodiments and modifications are examples of an information processing device and a medical image system according to the present invention, and are not intended to limit the present invention. The detailed configurations and operations of the components constituting the image forming apparatus can also be appropriately modified within the scope of the present invention.

In the above embodiment, the malignancy level map is created using variation in color according to the malignancy level, but a heatmap may be created according to the diagnosis difficulty at each position on the medical image.

The controller 31 of the imaging diagnosis support device 30 may specify diagnosis difficulty concerning the medical image for the medical image transmitted to the image management device 40. The controller 31 may add to the medical image with high difficulty a reason (comments) for setting "difficulty: high."

In the case where diagnosis difficulty is specified for the medical image transmitted from the imaging diagnosis support device 30, the image management device 40 may add a mark on the image with high difficulty when displaying the list of the medical images and call attention of the image interpretation doctor.

When displaying a form field of image interpretation opinions from the technician on the display of the console 20, the controller 31 of the imaging diagnosis support device 30 may pre-populate the field with the information obtained from the abnormality detection result for the medical image. The information input in the field of image interpretation opinions from the technician is managed in RIS 51.

The program(s) for executing each process in the devices may be stored in a portable recording medium. A carrier wave may also be applied as a medium providing the program data a communication line.

What is claimed is:

1. A medical image system comprising:
   an image management device;
   an information processing device interposed between an imaging control device and the image management device in communication,
   the information processing device including
     an abnormality detector that performs detection of an abnormality in a medical image received from the imaging control device; and
     a first hardware processor that determines, based on a result of the detection by the abnormality detector, content or a destination of transmission of the medical image or the result of the detection, wherein the first hardware processor determines a priority for displaying the medical image among a plurality of medical images based on the result of the detection, assigns the priority to the medical image, and transmits the medical image and the priority associated with the medical image to the image management device, and
   wherein the image management device includes:
     a storage that stores the plurality of medical images transmitted from the information processing device and priorities associated with the respective plurality of medical images; and
     a second hardware processor that determines an order of the plurality of medical images stored in the storage on a list to be displayed on a display based on the priorities associated with the plurality of medical images stored in the storage.

2. The medical image system according to claim 1, wherein the first hardware processor determines whether to send the medical image to the image management device based on the result of the detection.

3. The medical image system according to claim 1, wherein the first hardware processor determines, based on the result of the detection, a device to which the medical image or the result of the detection is transmitted.

4. The medical image system according to claim 1, wherein the first hardware processor determines a medical worker who is to be requested to interpret the medical image, based on the detection of the result and an attribute of the medical worker.

5. The medical image system according to claim 4, wherein the attribute of the medical worker includes at least one of a specialty, an image interpretation ability, a fatigue level, and availability.

6. The medical image system according to claim 1, wherein the abnormality detector generates data on at least one of a name of a lesion, a position of the lesion, a size of the lesion, a category of the lesion, a malignancy level, and a malignancy level map from the medical image.

7. The medical image system according to claim 1 further comprising:
   an additional examination determiner that presents necessity of an additional examination or re-imaging, and an item to be examined in the additional examination or the re-imaging concerning the medical image.

8. The medical image system according to claim 7, wherein the additional examination determiner presents at least one of a modality, a region to be imaged, and an imaging method.

\* \* \* \* \*